(12) United States Patent
Merrill

(10) Patent No.: US 7,105,711 B2
(45) Date of Patent: Sep. 12, 2006

(54) PROCESS FOR THE SELECTIVE HYDROGENATION OF PHENYLACETYLENE

(75) Inventor: James T. Merrill, Katy, TX (US)

(73) Assignee: Fina Technology, Inc., Houston, TX (US)

( * ) Notice: Subject to any disclaimer, the term of this patent is extended or adjusted under 35 U.S.C. 154(b) by 285 days.

(21) Appl. No.: 10/631,687

(22) Filed: Jul. 31, 2003

(65) Prior Publication Data

US 2005/0027149 A1    Feb. 3, 2005

(51) Int. Cl.
C07C 5/10    (2006.01)
(52) U.S. Cl. .................. 585/266; 585/261; 585/259
(58) Field of Classification Search ............. 585/266, 585/261, 259
See application file for complete search history.

(56) References Cited

U.S. PATENT DOCUMENTS

| | | | |
|---|---|---|---|
| 3,912,789 A | 10/1975 | Frevel et al. | |
| 4,101,451 A | 7/1978 | Frevel et al. | |
| 4,389,517 A | 6/1983 | Priddy et al. | |
| 4,440,956 A | 4/1984 | Couvillion | |
| 4,493,906 A | 1/1985 | Couvillion | |
| 4,822,936 A | 4/1989 | Maurer et al. | |
| 5,064,918 A | 11/1991 | Malanga | |
| 5,156,816 A | 10/1992 | Butler et al. | |
| 6,747,181 B1 * | 6/2004 | Bosman et al. ............. 585/259 |

FOREIGN PATENT DOCUMENTS

| | | |
|---|---|---|
| EP | 0584054 A1 | 2/1994 |
| WO | WO 02/055601 A1 | 7/2002 |

* cited by examiner

Primary Examiner—Thuan D Dang
(74) Attorney, Agent, or Firm—Tenley R. Krueger

(57) ABSTRACT

A process for the reduction of a phenylacetylene contaminant in the presence of a styrene monomer. A styrene monomer stream containing a minor amount of phenylacetylene is supplied to a hydrogenation reactor. A hydrogenation gas comprising hydrogen is also supplied to the hydrogenation reactor. The styrene monomer stream and the hydrogen are brought into contact with a catalyst bed containing a catalyst comprising a reduced copper compound on a theta alumina support. The hydrogenation reactor is operated at a temperature of at least 60° C. and a pressure of at least 30 psig to hydrogenate phenylacetylene to styrene. A product is recovered from the hydrogenation reactor having a substantially reduced phenylacetylene content and an enhanced styrene content. The hydrogenation gas comprises a mixture of nitrogen and hydrogen.

20 Claims, 2 Drawing Sheets

PROCESS FOR THE SELECTIVE HYDROGENATION OF PHENYLACETYLENE

FIELD OF THE INVENTION

This invention relates to the selective hydrogenation of phenylacetylene contaminants in styrene feedstocks and, more particularly, to the selective hydrogenation of such phenylacetylene contaminants in the presence of a copper-based hydrogenation catalyst under relatively high temperature and pressure conditions.

BACKGROUND OF THE INVENTION

Phenylacetylene is present in styrene monomer streams as an undesirable contaminant. Styrene monomer streams, which can include in addition to styrene various substituted styrenes, such as alphamethyl styrene and alkyl ring-substituted styrenes, are formed by the dehydrogenation of the corresponding alkylbenzene, such as ethylbenzene, to form the corresponding vinyl aromatic monomers, such as styrene in the case of ethylbenzene. An undesirable side reaction in such dehydrogenation processes occurs when the ethylbenzene is subjected to a severe dehydrogenation reaction to produce phenylacetylene. While the ethylbenzene, normally common in the resulting styrene product stream, can be readily removed by distillation, the fractional distillation of phenylacetylene and styrene can be accomplished only with difficulty.

In order to provide a purified styrene monomer stream for use in polymerization reactions, it is a conventional practice to selectively hydrogenate the phenylacetylene in the presence of the corresponding styrene monomer. Two types of catalysts may be employed in such phenylacetylene reduction procedures. One type of catalyst, such as disclosed in U.S. Pat. No. 5,156,817 to Butler et al and European Patent Application Publication No. 584,054, also to Butler et al, involves the selective hydrogenation of phenylacetylene over a palladium catalyst supported on an alumina carrier. The palladium catalyst is highly effective and permits the hydrogenation reaction to be carried out under relatively high temperature conditions of about 150° F. and also substantially elevated pressure conditions of about 60–70 psia. Another catalyst used in the selective hydrogenation of phenylacetylene is disclosed in U.S. Pat. No. 4,822,936 to Maurer et al. Here, the catalyst employed is reduced copper on a gamma alumina support. While the Maurer et al process offers the advantage of a catalyst which is less expensive than the palladium catalyst used in the Butler et al process, it also requires relatively modest temperature conditions as well as relatively low pressure conditions. In this respect, while Maurer discloses a hydrogenation temperature below 200° C., preferably in the range of 5° C. to about 100° C., the Maurer procedure is preferably limited to a hydrogenation temperature of less than 35° C. Even at this relatively low temperature, the Maurer procedure requires that the hydrogenation reaction be carried out at ambient or near ambient pressure conditions with a maximum pressure limited to 10 psig, i.e., less than about 25 pounds per square inch absolute.

SUMMARY OF THE INVENTION

In accordance with the present invention there is provided a process for the reduction of a phenylacetylene contaminant in the presence of a styrene monomer. In carrying out the invention a styrene monomer stream containing a minor amount of phenylacetylene is supplied to a hydrogenation reactor. A hydrogenation gas comprising hydrogen is also supplied to the hydrogenation reactor. Within the hydrogenation reactor the styrene monomer stream and the hydrogen are brought into contact with a catalyst bed containing a hydrogenation catalyst comprising a reduced copper compound on a theta alumina support. The hydrogenation reactor is operated at a temperature of at least 60° C. and a pressure of at least 30 psig to hydrogenate phenylacetylene to produce styrene. A product is recovered from the hydrogenation reactor having a substantially reduced phenylacetylene content and an enhanced styrene content. Preferably, the selective hydrogenation of phenylacetylene in the reactor is effective to convert at least 60% of the phenylacetylene in the styrene monomer stream to styrene. Preferably, the hydrogenation reactor is operated at a pressure within the range of about 45–150 psig at a temperature within the range of 60–80° C. It is also preferred that the hydrogenation component comprises a mixture of nitrogen and hydrogen in a mole ratio of hydrogen to nitrogen within the range of 0.2–2.0.

DETAILED DESCRIPTION OF THE INVENTION

Figure 1:
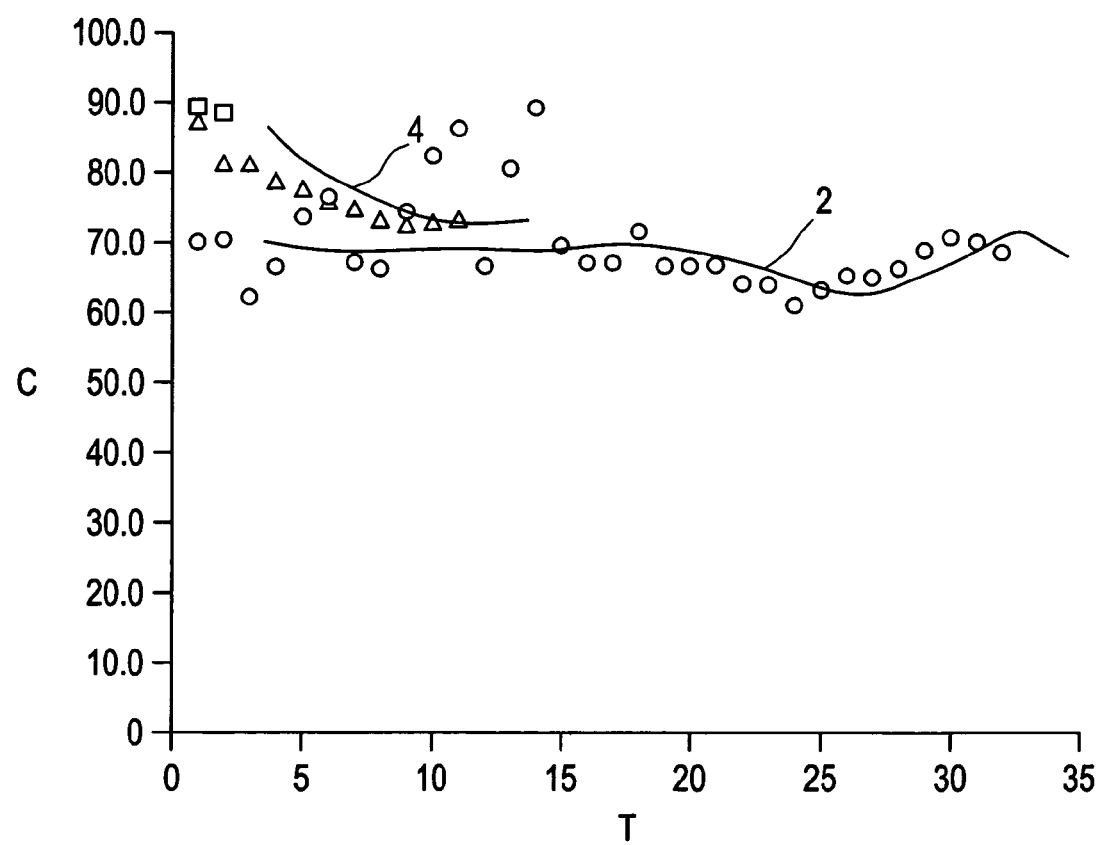
FIG. 1 is a graph illustrating phenylacetylene conversion for a catalyst system comprising a palladium-based catalyst and a catalyst system comprising copper on a theta alumina support in accordance with the present invention.

As noted previously, both palladium-based catalysts and copper-based catalysts have been employed in the hydrogenation of phenylacetylene in the presence of styrene monomer. The present invention will be described with respect to phenylacetylene and styrene. However, it is to be recognized that the invention can also be carried out with respect to substituted phenylacetylenes in the presence of the corresponding substituted styrene monomers. Such phenylacetylene and styrene pairs include vinyltoluene and tolacetylene, divinylbenzene and vinylacetylene.

The phenylacetylene reduction process described in the aforementioned patent to Butler et al involves the use of a palladium catalyst which can be employed under relatively severe dehydrogenation conditions to arrive at a very low phenylacetylene content in the resulting product. While this is highly desirable, palladium catalysts are relatively expensive. The aforementioned Maurer et al process offers the advantage of a relatively inexpensive copper catalyst but also requires relatively low temperature and pressure conditions. Even where the temperature is limited to 35° C., as in the preferred embodiment of the Maurer et al procedure, this procedure still requires that the pressure in the hydrogenated reactor be limited to atmospheric or near atmospheric.

The present invention proceeds in a manner contrary to the prior art teachings by employing a relatively inexpensive copper-based hydrogenation catalyst while permitting operations at relatively higher temperature and pressure conditions, for example, with temperatures ranging up to about 65° or 70° C. with pressures of several atmospheres, e.g., more specifically, 60–70 psia. The copper-based catalyst employed in the present invention may be derived by the reduction of a copper compound similarly as described in the Maurer patent, with the important distinction that the copper is supported on theta alumina rather than gamma alumina as required in Maurer et al.

The theta alumina-supported copper catalyst employed in the present invention can be prepared by any suitable technique. Typically, the catalyst is prepared by depositing a copper salt or copper oxide on a theta alumina support followed by reduction of the oxidized copper to metallic copper. A suitable theta alumina support can take the form of particulate alumina having an average particle size of about 1–4 mm. The particulate theta alumina is characterized by an x-ray powder diffraction corresponding to Joint Committee on Powder Diffraction standards #35–121, International Centre for Diffraction Data.

The oxidized copper used to form the catalyst precursor can be in the form of a powdered mixture of the theta-alumina and a copper oxide salt that are thoroughly mixed and subsequently extrudated to form catalyst particles. Alternatively, catalyst support particles formed from the theta-alumina can be impregnated with a copper containing aqueous solution such as cupric nitrate and nitric acid. Such procedures are well known to those skilled in the art of catalyst preparation.

The copper oxide or copper salt can be added to the support in any suitable amount depending upon the desired copper content of the final reduced catalyst. Typically, it will be desired to employ a catalyst in which the copper content is present in an amount of 5–25 wt. % based upon the composite of the support and the reduced catalyst. In order to reduce the catalyst to the form desired for use in the phenylacetylene reduction process, the catalyst precursor may be disposed in a suitable reduction vessel which is then purged with nitrogen in order to remove all air to provide a non-oxidizing environment. The reactor temperature can then be increased to a temperature to about 130° C. at a rate of about 50° C. per hour or less and then maintained at this temperature for a period of about one hour to allow the bed temperature to stabilize. The reactor temperature is then increased to a temperature of about 180° C. per hour or less. At this point, hydrogen is introduced into the inlet of the reactor in admixture with carbon monoxide so that the hydrogen concentration in the nitrogen stream is within the range of 0.5–1.0 mole percent. During this period the reactor inlet temperature is maintained at a value of about 180°–200° C. with the bed temperature monitored so that it does not exceed 230° C. Should the exotherm moving through the bed start to increase above 180° C., the hydrogen content in the inlet stream is reduced to maintain the exotherm as a maximum value of 230° C.

After the reaction front has passed through the reactor, the hydrogen concentration in the inlet stream is increased to about 2–3 mole % and the exotherm is again monitored to maintain the maximum temperature at about 230° C. At this point the copper in the theta alumina-supported catalyst should be completely reduced to the metallic form. This can be verified by increasing the bed temperature to 240° C. to check that no further reduction reaction is observed within the reactor.

In experimental work respecting the invention, a palladium catalyst of the type disclosed in the Butler '816 patent and a theta alumina-supported copper catalyst prepared in accordance with the above-identified procedure were employed in the selective hydrogen of phenylacetylene in a crude styrene stream. The theta alumina supported catalyst had a copper oxide content of 15 wt. %. The supported catalyst had a trilobe particle shape and an average cross-sectional dimension of 1.2 mm. The supported catalyst had a surface area of 60 m$^2$/g and a pore volume of 0.43 ml/g. The catalyst had a density of 0.77 kg/l. The results of the experimental work are illustrated in FIG. 1 in which the weight percent of the phenylacetylene conversion, C, is plotted on the ordinate versus the time on stream, T, in days of the test runs plotted on the abscissa. The experimental work was carried out in a linear reactor at a pressure of 125 psig with a hydrogen rate to provide a molar ratio of hydrogen to phenylacetylene of 16/1. The feed to the reactor in each case was a mixture of 60% styrene and 40% ethylbenzene containing 200 ppm phenylacetylene in the total reactor feed. The temperature in each case was controlled at about 150° F. at a pressure of about 125 psig. The tests were conducted at a liquid hourly space velocity (LHSV) of 60 hr.$^{-1}$. As indicated by data points ● and curve 2 of FIG. 1, the palladium catalyst (0.3 wt. % palladium on alumina) after discounting some initial wide swings in data, showed a phenylacetylene conversion rate of about 65 to 70 wt. %. As indicated by curve 4 (data points ▲), the copper-based catalyst, comprising 12 wt. % copper supported on theta alumina, showed an initial high conversion activity of about 80–85% which leveled off to a value slightly in excess of 70 wt. %. At the end of two weeks, the test was terminated because of an unusually large pressure drop in the reactor. As indicated by data points ■, a second test based upon the copper catalyst was started, but this was shut down after a period of a few days after a large pressure drop developed in the reactor. Although the cause of the pressure drop is unknown, an inspection of the catalyst screens showed a green color typical of the copper-based catalyst, indicating possible plugging of the screens within the reactor. While the copper-based catalyst used in the experimental work appeared to be mechanically fragile in the test reactor, the test results illustrated in FIG. 1 clearly show that the theta alumina-supported copper catalyst can be employed in phenylacetylene reduction at temperatures associated with the temperatures used with a palladium-based catalyst. This is accomplished at a substantially lower cost than when employing the palladium catalyst.

Figure 2:
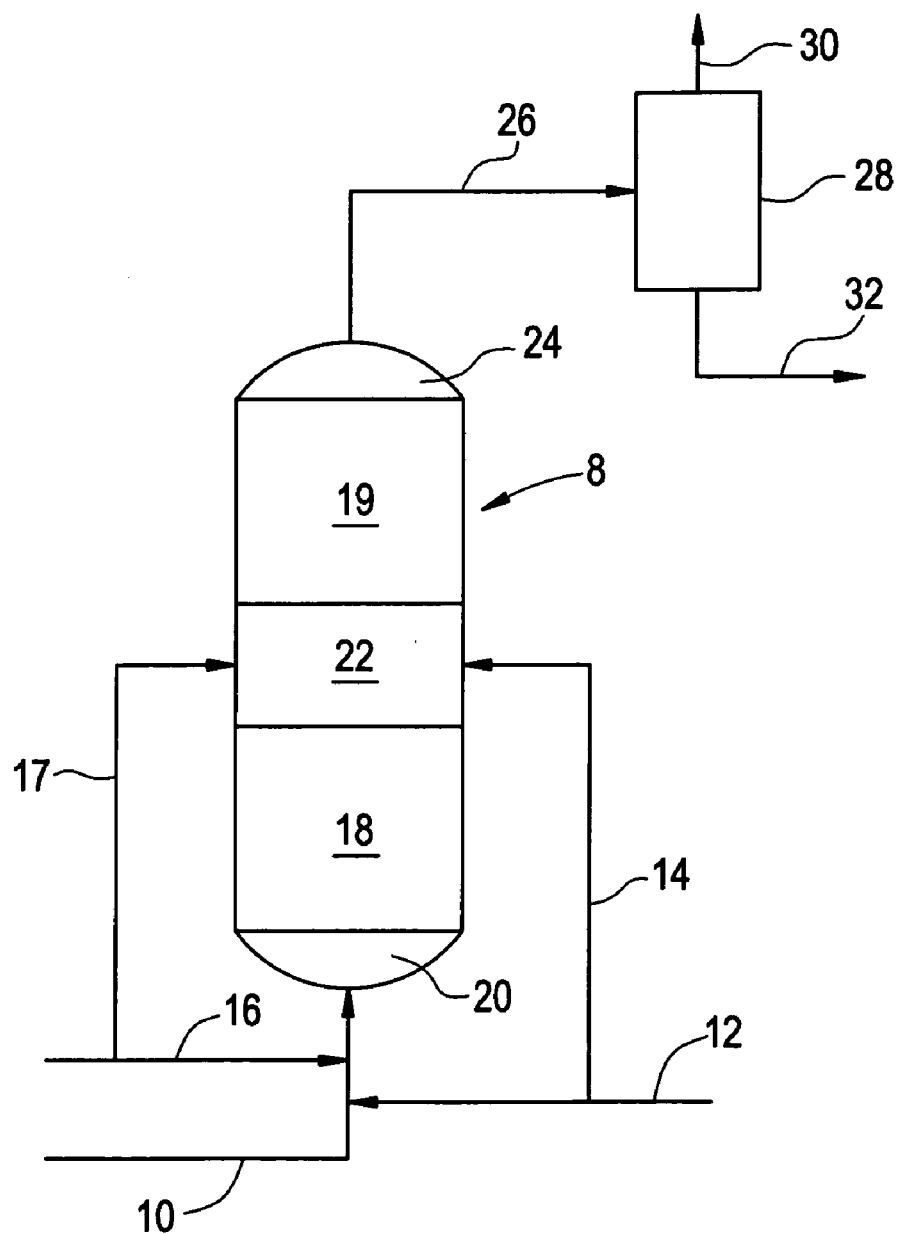
FIG. 2 is a schematic illustration of an up-flow, multistage reactor suitable for use in carrying out the present invention.

While the invention may be carried out in any suitable reactor system, a preferred application of the invention is in a multistage upflow reactor which involves the interstage injection of the hydrogenation gas. A preferred application is in the use of a two-stage reactor system of the type described in the aforementioned patent to Butler. Such a reactor system is illustrated in FIG. 2 of the drawings. As shown in FIG. 2, a reactor 8 is supplied via line 10 with a crude styrene stream containing phenylacetylene through a suitable heat exchanger (not shown) effective to bring the styrene stream to the desired operating temperature. The styrene stream is mixed with a hydrogenation gas comprising hydrogen, a mixture of hydrogen and nitrogen, or a mixture of hydrogen, nitrogen, and carbon monoxide, such as disclosed in the aforementioned U.S. Pat. No. 5,156,816 to Butler. The hydrogenation gas is supplied via line 12 to the input side of reactor 8 and also to an intermediate zone of reactor 8 by line 14. A diluent gas, such as nitrogen, is also supplied to the input side of the reactor via line 16 and into the intermediate zone of the reactor 8 via line 17.

The reactor comprises two stages 18 and 19, each containing the theta alumina-supported copper catalyst employed in the present invention. The reactor further comprises an inlet plenum 20, an interstage injection plenum 22, and a withdrawal plenum 24. The interstage injection plenum 22 may be filled with a suitable particulate refractory material, such as alumina balls, which provides for diffusion of the hydrogenation gas and the styrene stream between the two catalysts stages. While two catalyst stages are illustrated, it is to be recognized that three or more catalyst stages also can be employed in carrying out the present invention. Also, separate reactors, as discussed in the Butler '816 patent, can be employed. The diluent gas supplied via lines 16 and 17 may take the form of nitrogen. The product stream withdrawn from the reactor 8 is supplied through line 26 to a low pressure separator 28 from which volatile components are withdrawn via line 30 and a bottoms fraction comprising the purified styrene withdrawn via line 32.

The styrene supplied to the reactor via line 10 typically will be recovered from an ethylbenzene dehydrogenation reactor which provides an output having a major component of styrene, a minor but still significant component of ethylbenzene, and a low concentration (less than 1 volume percent) of phenylacetylene. The ethylbenzene is removed from the styrene through a suitable fractionation column which, as described previously, is effective in removing ethylbenzene but leaves substantial amounts of the original phenylacetylene content present in the styrene stream. Thus, the styrene stream actually supplied to reactor 8 will normally contain about 50–75% styrene and about 40–150 ppm phenylacetylene. The phenylacetylene content for such a styrene stream can be reduced through the selective hydrogenation process of the present invention to levels of about 10 ppm or less.

As noted previously, the hydrogenation gas supplied via line 12 can comprise hydrogen, hydrogen mixed with nitrogen, or hydrogen mixed with hydrogen and carbon monoxide. Preferably, the hydrogenation gas will comprise mixtures of nitrogen and hydrogen in a mole ratio of nitrogen to hydrogen within the range of 0.2–2.0. Preferably, the nitrogen to hydrogen mole ratio will be within the range of about 0.5–1.5. Where carbon monoxide is employed, it usually will be present in an amount within the range of about 1–5 mole percent.

While it will be preferred in carrying out the present invention to utilize a multistage upflow reactor of the type depicted in FIG. 2, it will be recognized that other suitable reactor and recovery systems, such as those disclosed in the aforementioned U.S. Pat. No. 5,156,816, may be employed. For a further description of such systems, reference is made to the aforementioned U.S. Pat. No. 5,156,816 to Butler et al, the entire disclosure of which is incorporated herein by reference.

As noted previously, the hydrogenation reactor is operated at a temperature of at least 60° C. and a pressure of at least 30 psig. Preferably, the reactor is operated under conditions effective to convert at least 60% of the phenylacetylene in the styrene stream to styrene. Preferably, conversion of at least 70% of the phenylacetylene in the styrene stream is converted to styrene over a substantial portion of the catalyst during the catalyst run prior to regeneration.

As indicated by the previous experimental work, the dehydrogenation reaction can be carried out at a relatively high space velocity. Preferably the space velocity (LHSV) is at least 30 hrs.$^{-1}$. Typically, a load of catalysts in the hydrogenation reactor can be used until the activity of the catalyst in terms of phenylacetylene conversion falls to less than 40 wt. % of the phenylacetylene in the styrene stream. At this stage the reactor can be taken off stream and the catalyst replaced.

Having described specific embodiments of the present invention, it will be understood that modifications thereof may be suggested to those skilled in the art, and it is intended to cover all such modifications as fall within the scope of the appended claims.

What is claimed is:

1. A process for the reduction of phenylacetylene in the presence of a styrene monomer comprising:
   (a) supplying a styrene monomer stream containing a minor amount of phenylacetylene to a hydrogenation reactor;
   (b) supplying a hydrogenating gas comprising hydrogen to said hydrogenation reactor;
   (c) within said hydrogenation reactor, flowing said styrene monomer stream and said hydrogen into contact with a catalyst bed containing a hydrogenation catalyst consisting essentially of metallic coppper on a theta alumina support;
   (d) operating said reactor at a temperature of at least 60° C. and a pressure of at least 30 psig to hydrogenate phenylacetylene to produce styrene; and
   (e) recovering a product from said hydrogenation reactor having a reduced phenylanetylene content and an enhanced styrene content.

2. The method of claim 1 wherein the selective hydrogenation of phenylacetylene in said reactor is effective to convert at 60% of the phenylacetylene in said reactor input stream to styrene.

3. The method of claim 1 wherein said hydrogenation reactor is operated at a pressure within the range of 45–150 psig.

4. The method of claim 1 wherein said hydrogenation reactor is operated at a temperature within the range of 60–80° C.

5. The method of claim 1 wherein said hydrogenation component comprises a mixture of hydrogen and nitrogen.

6. The method of claim 5, wherein the mole ratio of nitrogen to hydrogen in said mixture is within the range of 0.2–2.0.

7. The method of claim 6, wherein the mole ratio of nitrogen to hydrogen in said mixture is within the range of 0.5–1.5.

8. The method of claim 1, wherein said hydrogenation gas comprises a mixture of nitrogen, hydrogen and carbon monoxide.

9. The method of claim 8, wherein said carbon monoxide is present in an amount within the range of about 1–5 mole % of said mixture.

10. The method of claim 9 wherein the mole ratio of nitrogen to hydrogen in said mixture is within the range of 0.5–1.5.

11. Tho method of claim 1, wherein said styrene monomer steam contains less than 1 volume % of phenylacetylene.

12. The method of claim 11 wherein the styrene monomer stream supplied to said reactor contains phenylacetylene in an amount within the range of 40 –150 ppm.

13. The method of claim 12, wherein the product recovered from said hydrogenation reactor contains phenylacetylene in an amount of about 10 ppm or less.

14. The method of claim 8, wherein the selective hydrogenation of phenylacetylene in said reactor is effective to convert at least 70% of the phenylacetylene in the styrene monomer stream to styrene.

15. A process for the reduction of phenylacetylene in the presence of a styrene monomer in a multistage hydrogenation reaction zone comprising at least two catalyst stages and intermediate injection zone between said stages comprising:

supplying a styrene monomer stream containing a minor amount of phenylacetylene to said multistage hydrogenation reaction zone;

supplying a hydrogenating gas comprising hydrogen to said hydrogenation reaction zone;

within said hydrogenation reaction zone, flowing said styrene monomer stream and said hydrogenation gas into contact with catalyst beds in said catalyst stages containing a hydrogenation catalyst consisting essentially of metallic copper on a theta alumina support;

operating said reaction zone at a temperature of at least 60° C. and a pressure of at least 30 psig to hydrogenate phenylacetylene to produce styrene; and recovering a product from said hydrogenation reactor having a reduced phenylacetylene content and an enhanced styrene content.

16. The method of claim 15, wherein said styrene monomer stream and said hydrogenating gas are supplied to the first stage of said multistage reaction zone and separately into the intermediate injection zone between said catalyst stages and into said second stage of said multistage reaction zone.

17. The method of claim 16 wherein said hydrogenation gas comprises a mixture of hydrogen and nitrogen.

18. The method of claim 17, wherein the mole ratio of nitrogen to hydrogen in said mixture is within the range of 0.2–2.0.

19. The method of claim 15, wherein said hydrogenation gas comprises a mixture of nitrogen, hydrogen and carbon monoxide.

20. The method of claim 19, wherein said carbon monoxide is present in an amount within the range of about 1–5 mole % of said mixture.

* * * * *